United States Patent
Moellmann et al.

(10) Patent No.: US 7,557,091 B2
(45) Date of Patent: Jul. 7, 2009

(54) HKI10311129, NOVEL ANTIBIOTIC, METHOD FOR PRODUCING THE SAME AND THE USE THEREOF

(75) Inventors: Ute Moellmann, Jena (DE); Kerstin Herold, Jena (DE); Martin Roth, Jena (DE); Ingrid Groth, Jena-Wogau (DE); Friedrich Gollmick, Jena (DE); Udo Graefe, Jena (DE); Karin Brigitte Charlotte Graefe, legal representative, Jena (DE); Andrea Graefe, legal representative, Rosdorf (DE); Susanna Graefe, legal representative, Jena (DE)

(73) Assignee: Leibniz-Institut fuer Naturstoff-Forschung und Infektionsbiologie e.V. Hans-Knoell-Institut, Jena (DE)

( * ) Notice: Subject to any disclaimer, the term of this patent is extended or adjusted under 35 U.S.C. 154(b) by 576 days.

(21) Appl. No.: 11/497,953

(22) PCT Filed: Feb. 2, 2005

(86) PCT No.: PCT/DE2005/000186

§ 371 (c)(1),
(2), (4) Date: Aug. 2, 2006

(87) PCT Pub. No.: WO2005/082878

PCT Pub. Date: Sep. 9, 2005

(65) Prior Publication Data

US 2006/0270617 A1 Nov. 30, 2006

(30) Foreign Application Priority Data

Feb. 27, 2004 (DE) .................... 10 2004 010 219

(51) Int. Cl.
*A61K 31/70* (2006.01)
(52) U.S. Cl. .............................. 514/34; 514/33; 514/25; 536/4.1
(58) Field of Classification Search .................. 514/34, 514/33, 25; 536/4.1
See application file for complete search history.

(56) References Cited

FOREIGN PATENT DOCUMENTS

DE 100 65 606 6/2002
JP 06339395 12/1994

OTHER PUBLICATIONS

Aug. 4, 2004 "Biosynthesis of cervimycin C, an aromatic polyketide antibiotic bearing an unusual dimethylmalonyl moiety" Kerstin Herold, et al., The Royal Society of Chemistry 2004, pp. 2411-2414.
Apr. 12, 2003 "CDC reports first case of vancomycin resistant, *Staphylococcus aureus*" Scott Gottlieb, BMJ, vol. 326 p. 783.
Dec. 2, 1992 "Dutomycin, a new Anthracycline Antibiotic From *Streptomyces*" The Journal of Antibiotics, vol. 45, No. 12, pp. 1-3.
Aug. 11, 1997 "Polyketomycin, a New Antibiotic from *Streptomyces* sp. MK277-AF1; I. Taxonomy, Production, Isolation, Physicochemical Properties and Biological Activities", Isao Momose, et al., The Journal of Antibiotics, vol. 51, No. 1, pp. 21-25.
Aug. 11, 1997 "Polyketomycin, a New Antibiotic from *Streptomyces* sp. MK277-AF1; II. Structure Determination", Isao Momose, et al., The Journal of Antibiotics, vol. 51, No. 1, pp. 26-31.

*Primary Examiner*—Shaojia Anna Jiang
*Assistant Examiner*—Michael C. Henry
(74) *Attorney, Agent, or Firm*—Jordan and Hamburg LLP

(57) ABSTRACT

The invention relates to the novel antibiotic HKI10311129 which has a molecular weight of 1113 and the summation formula $C_{56}H_{75}NO_{22}$. The invention also relates to a method for producing said antibiotic using the microorganism *Streptomyces* spec. DSM 13059, and to the use thereof as an antibacterial substance which is especially effective against infections with Gram positive bacteria, especially antibiotic-resistant germs.

4 Claims, No Drawings

HKI10311129, NOVEL ANTIBIOTIC, METHOD FOR PRODUCING THE SAME AND THE USE THEREOF

BACKGROUND OF THE INVENTION

It is common knowledge that pathogens of bacterial infectious diseases become resistant under the influence of antibiotic therapy under selection pressure, among other reasons also more quickly for a false and too frequent administration of antibiotics. Special problems have been increasingly caused by infections that are provoked by multiresistant gram-positive bacteria, such as *staphylococcus aureus*, or by glycopeptide-resistant enterococci; in case of hospitalism, in patients whose immune system is undermined they can lead to serious diseases. The multiresitances developed in these germs make the treatment more difficult because therapeutic agents do not exist any longer. Vancomycin (a glycopeptide) is the reserve antibiotic to treat serious infections with multiresistant staphylococci (MRSA). Up to now, the vanA-type vancomycin resistance has only been observed in enterococci (VRE) without the extreme multiresistant problem like in MRSA. The interspecific transfer of the vanA-type resistance of enterococci to staphylococci, which has been feared for a long time, occurred in the USA in 2002 for the first time. In these *staphylococcus aureus* strains that are highly resistant against vancomycin the vanA gene is integrated into a multiresistant plasmid (Gottlieb, S. BMJ 326; 783(2003)).

These developments and the partly underestimated necessity for intensive searches for new structures and targets have led to a lack of sufficiently effective therapeutic agents. To ensure the curing of bacterial diseases and to be able to treat infections with resistances against antibiotics, new substances with antibiotic effects are urgently required (see for example Gräfe, Biochemie der Antibiotika (Biochemistry of antibiotics), Spektrum Heidelberg 1992; S. Grabley, R. Thiericke & U. Gräfe, Drug Discovery from Nature, Springer, S. 281-301, 1999). For the just explained reason, new antibiotics that can overcome the described resistance barriers become more and more important. In addition to this, other disadvantages such as the insufficient scope of efficiency, unfavorable pharmacokinetics and the side effects of the currently available antibiotics should be overcome.

Therefore, it is the object of the present invention to make a new microbial agent with an original structure and good anti-microbial characteristics, against multiresistant germs in particular, available.

According to the invention, this task is fulfilled by the fact that the actinomycete strain *streptomyces* sp. HKI 0179 is fermented in a liquid growth medium with carbon and nitrogen sources as well as usual inorganic salts till the new antimicrobial agent, hereinafter referred to as HKI10311129, accumulates in the culture solution and can be isolated from it in a pure form afterwards. The streptomyce strain KI 0179 was deposited as DSM 13059 at the Deutschen Sammlung für Mikroorganismen und Zellkulturen (DSMZ) (German Collection for Microorganisms and Cell Cultures) in Braunschweig, Mascheroder Wege 1.

The difference between HKI10311129 and the antibiotics known till now is the innovative character of the chemical structure of HKI10311129 that has been demonstrated by physicochemical measurements without doubt. (Tables 1 and 2).

Antimicrobial effects are not known for related structures that are described in the Japanese patent 94 339 395, in CA 122, 237919g and in J. Antibiot., 45 (1992), 1974-6. For a further related structure, described in J. Antibiot. 51 (1998), 21-25, 26-32, an activity against methicillin resistant staphylococci is certainly known, but an activity against enterococci and particularly against strains with a vanA-type vancomycin-resistance is not known.

Although the antibiotic altamiramycin has already been known from the streptomyce strain DSM 13059 (DE 100 65 606), the new antimicrobial agent HKI10311129 has been discovered now. It has a surprisingly strong antibacterial effect against gram-positive bacteria, against multiresistant germs such as staphylococci and enterococci in particular. HKI10311129 can be particularly used for men and animals as a medicine against infections with multiresistant gram-positive germs, the ones with a vanA-type glycopeptide resistance included.

SUMMARY OF THE INVENTION

Thus, the invention relates to:

1. A compound of the molar mass 1113, the total formula $C_{56}H_{75}NO_{22}$, the structural formula:

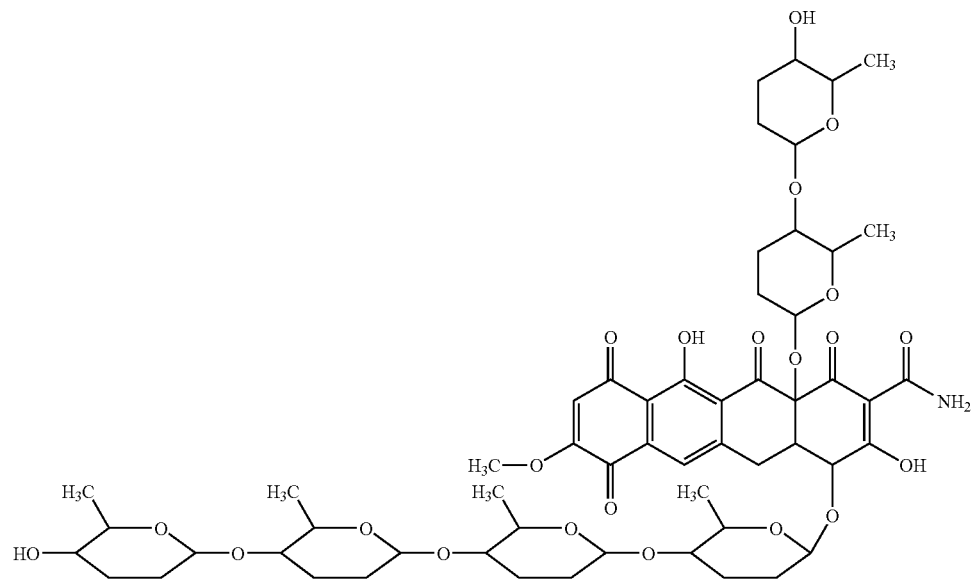

and the physicochemical characteristics, called HKI10311129, indicated in the Tables 1 and 2.

2. Medicaments, containing HKI10311129 together with usual carrier substances and additives, described for example in "Remington's Pharmaceutical Sciences Handbook, Hack Pub. co., N.Y., USA", or in Remington: The Science and Practice of Pharmacy by Alfonso R. Gennaro (Editor), A. L. Gennaro, or in the Handbook of Pharmaceutical Additives, Second Edition Pharmaceutical Additives Electronic Handbook—2002, Handbook of Pharmaceutical Additives, Second Edition Book and CD, Michael and Irene Ash. The anti-infective compounds can be prepared in such a way that they can be used as a solution or suspension in pharmaceutically acceptable media for a topic or parenteral application, via intravenous, subcutaneous or intramuscular injections, for intranasal application; as a pill, capsule or suppository. The compounds can be administered in doses ranging from 0.1 to 1000 mg/kg of the body weight.

3. A procedure for manufacturing HKI10311129, wherein *streptomyces* sp. DSM 13059 is cultivated in a growth medium until HKI10311129 accumulates in the culture solution and is afterwards separated out of it.

4. The use of HKI10311129 as a pharmacologically effective substance, particularly as an antibiotic, especially against multiresistant and vancomycin resistant bacteria.

In the following, the invention is described in detail, in particular in its preferred embodiments. Furthermore, it is determined by the contents of the claims.

DETAILED DESCRIPTION OF THE INVENTION

Definitions:
The inventive compound is designated as HKI10311129.
The technical term culture solution stands for the growth medium that contains the *streptomycete mycelium*.

The inventive antibiotic HKI10311129 is produced by a *streptomyces* sp. strain, an isolate of the "Grotta dei Cervi" in South of Italia. This strain is characterized by specific features (see below).

Thanks to subsequent isolation steps a colony was isolated from *streptomyces* sp. DSM 13059 that accumulates the antibiotic HKI10311129 in an exceptionally efficient way within the culture solution. An isolate of *streptomyces* sp. was deposited with the registration number DSM 13059 at the Deutschen Sammlung für Mikroorganismen und Zellkulturen GmbH in Braunschweig, Mascheroder Weg 1B, 38124 Braunschweig, Germany, on 24 Sep. 1999 according to the conditions of the Budapest Treaty. It can be characterized as follows: LL-DAP in peptidoglycan, spore carrier of type S, open spirals, mainly short 34, max. 6-7 windings and RA loops, straight loops, big spores, no melanin formation, dissoluble brown pigment on all ISP media, dense aerial mycelium with grayish spore, brown-brownish black, on ISP reddish violet substrate mycelium, very good growth and sporulation on all ISP media.

In a medium with a carbon source, a nitrogen source and usual mineral salts, *streptomyces* sp. DSM 13059 produces the inventive compound HKI10311129. Instead of the strain DSM 13059, its variants and mutants can also be used. Only those kinds of microorganisms of the species are considered variants and mutants that are capable to synthesize the inventive compounds.

Such variants and mutants can also be produced in commonly known procedures by physical means, for example by radiation with ultraviolet or X-rays or by chemical mutagens.

The screening for mutants and variants, which synthesize the inventive compound, can be performed by determining the biological activity of the active substances accumulated within the cultural solution, for example by testing the antibiotic effect on known test germs in methods known to the experts and by chromatographic identification.

Carbohydrates that can be assimilated and sugar alcohols, such as glucose, lactose, maltose, glycerol, mannite or their mixtures as well as natural products containing carbohydrates, such as malt extract or molasses, are preferably used as a carbon source.

Amino acids, peptides and proteins as well as their decomposition products, for example tryptones or peptones, moreover meat extracts, ground seed, for example of maize, wheat, beans, soybeans or cotton plants, distillation residues of alcohol production, fish meals or yeast extracts, are suitable as nitrogen sources.

The cultivation is done in an aerob manner, for example submers by shaking or stirring in Erlenmeyer flasks or fermenters, if required combined with the supply of air or oxygen.

The fermentation can be performed for example in steep chest bottles, Erlenmeyer or round flasks of different volumes, in glass fermentors or V2A steel tanks.

It is carried out at a temperature of between 15° C. and 37° C. and for a ph-value of between 4 and 8.

The microorganism is cultivated under these conditions during 3-6 days.

The fermentation can be performed on the laboratory scale (culture volumes of between 100 ml and 200 ml), but also in the production scale (volumes of up to several m$^3$).

The cultivation is advantageously performed in several stages, that means that first one or more pre-cultures are produced in a liquid growth medium and then they are inoculated into the real production medium, the main culture, for example at a ratio of 1:15-1:20.

The pre-culture can be obtained by transferring spore-containing mycelium of e.g. an oatmeal growth medium into a culture solution, for example by inoculating agar pieces covered by mycelium, and then they are incubated for one or two days.

The spore-containing mycelium can be obtained for example by growing the strain on a culture medium, such as oatmeal agar or soyflour glucose agar, for about 7-10 days.

The antibiotic HKI10311129 is contained in varying portions in the culture solution as well as preferably in the mycelium.

To test the concentration of the agent within the culture medium or in the sinlge isolation stages, the usual methods for determining the biological activity known by the experts can be used, for example the agar diffusion punch plate test.

For the thin-film chromatographic separation, the detection can be performed by different coloring agents (such as vanillin sulfuric acid). The isolation of the antibiotic HKI10311129 from the culture solution and the mycelium is done by known methods considering the chemical, physical and biological characteristics of the products.

To isolate the antibiotic HKI10311129 from submerse culture preparations, the culture medium and mycelium are separated at the end of the fermentation and the mycelium is extracted by organic solvents, such as methanol or acetone, preferably methanol.

Further amounts of HKI10311129 are gained by extracting the culture solution separated from the mycelium by means of water-insoluble solvents, e.g. ethyl acetate.

After the concentration of the extracts and possibly the re-extraction of the concentrated methanol extract of the mycelium by means of water-insoluble organic solvents, such as ethyl acetate or dichloromethane, the antibiotic HKI10311129 is isolated by using usual chromatographic adsorbents or carrier materials, e.g. silica gel or organophilic dextrangels.

Pure HKI10311129 is finally obtained by the sequential application of the column chromatography at silica gel, of the gel-permeation chromatography at organophilic dextrangels by using polar organic solvents, such as methanol, of the medium-pressure chromatography at silica gel $RP_{18}$ by using acetonitril/water mixtures as well as of the high-performance liquid chromatography by using methanol/water.

The chemical identity of the antibiotic HKI10311129 is proven by the results obtained in the high-resolution mass spectrometry (FAB-MS, Quadrupol-Electrospray-MS, CID-MS/MS) as well as by the high-resolution 600 MHz proton spectroscopy and the 150 MHz-$^{13}$C-NMR correlation spectroscopy.

The antibacterial effects of HKI10311129 can be determined by applying methods well-known to the experts, such as the agar plate diffusion test and the determination of the minimal inhibitory concentration (MIC).

HKI10311129 is effective against bacteria, preferably against gram-positive bacteria, for example *bacillus subtilis* ATCC 6633, *staphylococcus aureus* SG 511, *staphylococcus aureus* 134/93 (multiresistant) and *enterococcus faecalis* 1528 (vanA-type vancomycin resistance).

Due to its extremely valuable, antibacterial characteristics, the invented antibiotic HKI10311129 is very well suited to be used as an antimicrobial therapeutic agent, particularly in the application against vanA-type resistant risk germs, such as vanA-type resistant enterococci as well as multiresistant and vanA-type vancomyin resistant staphylococci that have developed in the meantime.

The inventive antibiotic HKI10311129 can be administered as a substance or as a pharmaceutical preparation with suited additives or carrier material known to the experts. The preparations are produced in a familiar manner by using the standard additives and carrier materials, described for example in the "Remington's Pharmaceutical Sciences Handbook, Hack Pub. co., N.Y., USA".

The pharmaceutical preparations can be medicaments that are to be administered orally, e.g. pills, capsules and coated tablets, percutan kinds of preparation, e.g. ointments or sprays, transdermal therapeutic systems (TTS) or gels, intranasal kinds of preparations such as nose spray or nose drops, rectal kinds of preparation such as suppositories, and parenteral medicaments, e.g.: implants, pressed preparations and ampoules. The inventive medicaments are generally administered orally or parenterally, but a rectal application is also possible. Suited solid or liquid galenic preparations are for example pellets, powder, pills, coated tablets, suspensions.

Antimicrobial characteristics of HKI10311129:

The antimicrobial characteristics have been tested according to the US laboratory standards—National Committee for Clinical Laboratory Standards, Methods for dilution antimicrobial susceptibility tests for bacteria that grow aerobically, Approved Standard M7-A. NCCLS, Villanova, Pa., 1991). The determined MIC values are given in Table 3.

TABLE 1

Physicochemical characteristics of HKI10311129

| Characteristics | yellow-orange amorphous substance |
|---|---|
| Molecular weight | 1113 |

TABLE 1-continued

Physicochemical characteristics of HKI10311129

| | |
|---|---|
| HRESI-MS ([M+Na]$^+$) | 1136.4707(ber. 1136.4678 for $C_{56}H_{75}NaNO_{22}$) |
| Formula | $C_{56}H_{75}NO_{22}$ |
| IR spectrum $\lambda_{max}$ (cm$^{-1}$) | 858, 916, 997, 1053, 1112, 1163, 1225, 1247, 1351, 1377, 1448, 1592, 1625, 1686, 2853, 2922, 3417 |
| $[\alpha]_D$ | +15.1° |
| UV-VIS spectrum | |
| $\lambda_{max}$ in nm ($\epsilon$ in M$^{-1}$cm$^{-1}$) | 242(15013.3); 434(1975.7) |
| Melting point: | 155-159° C. |

TABLE 2

$^{13}$C and $^1$H signals in the NMR spectrum of HKI10311129
(in CDCl$_3$; chemical dislocation in ppm;
multiplicity: m: multiplet, s: singlet; d: dublet; q: quarterner;
br: broad*: Proton signals cannot be assigned due to superpositions))

| $\delta_C$ | $\delta_H$ |
|---|---|
| 17.09 | 1.15d |
| 17.14 | 1.09d |
| 17.19 | 1.09d |
| 17.98 | 0.70 d |
| 18.10 | 1.25 d |
| 18.26 | 1.20 d |
| 22.66 | 1.28m/* |
| 23.60 | 1.88 m/1.65 m |
| 24.44 | * |
| 24.65 | 1.88m/1.60m |
| 24.65 | 2.05m/1.70m |
| 24.79 | 1.40m/* |
| 27.81 | 3.83m/3.50m |
| 29.68 | 1.34m/1.24m |
| 30.04 | 2.17m/* |
| 30.20 | * |
| 30.86 | 2.00m/1.55m |
| 30.98 | 1.81m/1.55m |
| 31.20 | 1.41m/* |
| 43.02 | 3.08m |
| 56.71 | 3.90s |
| 66.75 | 4.04m |
| 66.75 | 3.86m |
| 66.94 | 3.93m |
| 67.50 | 3.56brs |
| 71.34 | 3.23m |
| 72.18 | 4.32d |
| 74.40 | 4.04m |
| 74.56 | 3.00m |
| 74.93 | 3.31m |
| 75.13 | 3.08m |
| 75.79 | 3.20m |
| 78.75 | 3.07m |
| 79.60 | 3.08m |
| 85.36 | q |
| 99.16 | 4.78s |
| 99.39 | 4.80s |
| 99.58 | 4.80s |
| 99.75 | 4.55dd |
| 101.04 | q |
| 102.23 | 4.63dd |
| 102.95 | 4.42dd |
| 110.46 | 6.11s |
| 112.74 | q |
| 120.36 | 7.52s |
| 124.85 | q |
| 133.53 | q |
| 152.81 | q |
| 160.29 | q |
| 163.16 | q |
| 173.63 | q |
| 179.11 | q |

TABLE 2-continued $^{13}$C and $^1$H signals in the NMR spectrum of HKI10311129
(in CDCl$_3$; chemical dislocation in ppm;
multiplicity: m: multiplet, s: singlet; d: dublet; q:
quarterner;
br: broad*: Proton signals cannot be assigned due to
superpositions))

| $\delta_C$ | $\delta_H$ |
|---|---|
| 189.29 | q |
| 189.60 | q |
| 190.36 | q |
| 193.92 | q |

TABLE 3

Antimicrobial activity of the antibiotic HKI10311129:

| Test organism | MIC values (µg/ml) |
|---|---|
| staphylococcus aureus SG 511 | 0.8 |
| staphylococcus aureus 134/93 (MRSA) | 0.8 |
| enterococcus faecalis 1528 (VRE) | 0.4 |
| bacillus subtilis ATCC 6633 | <0.05 |

EXAMPLES OF THE INVENTIVE PROCEDURE

1. Fermentation of *streptomyces* sp. DSM 13059
1a. Cultivation conditions for *streptomyces* sp. DSM 13059:
   To gain a mycelium with good sporangia, *streptomyces* sp. DSM 13059 is cultivated on a growth medium of the following composition at 28° C. for 6 days (g/l):oatmeal 20, agar 20, pH 6.8-7.0 (sterilization at 110° C. for 25 min.).
1b. Preparation of a pre-culture of the strain DSM 13059: 1 agar-mycelium piece (surface of 1-2 cm$^2$) of the source culture, which has been cultivated according to 1a, is used to inoculate 100 ml of a pre-culture medium composed as follows (g/l): Soybean flour 15, glucose 15, NaCl 5, CaCO$_3$ 1, KH$_2$PO$_4$ 3, (pH 6.5 after sterilization at 110° C. for 25 min.) in 500 ml Erlenmeyer flask. The inoculated pre-cultures are cultivated at 28° C. for 48 hours.
1c. Preparation of a production culture of the strain DSM 13059: 5 ml of this pre-culture are used to inoculate 500 ml Erlenmeyer flask with 100 ml of the production medium composed as follows: mannite 20, soybean flour 20, pH 6.5 (after sterilization at 115° C. for 25 min). The cultivation is performed at 28° C. and with 180 r/min on a circular swivel table.
2. Extraction of the antibiotic HKI 10311129 from the culture solution The culture solution according to example 1 is fractionated by separating it into mycelium and culture filtrate. The former is extracted with methanol. The extract is diluted with the fourfold volume of water and extracted with ethyl acetate. The culture filtrate is also extracted in the ratio 2:1 (aqueous phase to ethyl acetate). The ethyl acetate extracts are combined, dried over sodium sulphate and concentrated in vacuum to dryness. Chromatographic clarification of HKI 10311129: The remaining brown, oily residue is absorbed in a little bit of chloroform and the solution is filtered. By the addition of hexane (20-fold volume) a crude product is precipitated. The further clarification is performed by gel permeation chromatography at Sephadex LH-20 by using methanol as an eluent. The center fraction providing the antibacterial effect is combined and concentrated to dryness in vacuum.

By using a chloroform-methanol gradient (100:0; 95:5; 9:1) the silicagel chromatography is used for the fine clarification. The yellow fraction with the antibiotic effect is concentrated to dryness. Highly pure HKI 10311129 can be obtained by chromatography at reverse phase silica gel by using a slightly acid eluent (e.g. MeCN-H$_2$O; 83:17 and 0.05% trifluor ethanoic acid).

The invention claimed is:

1. Compound (HKI10311129) having a molar mass 1113 and an empirical formula $C_{56}H_{75}NO_{22}$, and a structural formula as follows:

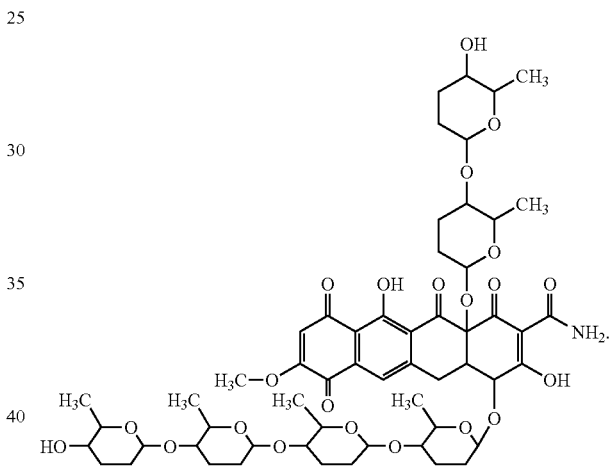

2. Medicament comprising the compound of claim 1 and at least one pharmaceutically acceptable carrier and/or additive.

3. A method for producing HKI10311129, comprising cultivating *streptomyces* sp. DSM 13059 in a growth medium to form a culture solution containing HKI10311129 and thereafter isolating HKI10311129 from the culture solution.

4. Method of treating a patient infected with a bacterial infectious disease, comprising administering to the patient a compound or medicament according to claim 1 or 2.

* * * * *